(12) United States Patent
Shibata et al.

(10) Patent No.: US 7,271,892 B2
(45) Date of Patent: Sep. 18, 2007

(54) METHOD AND APPARATUS FOR INSPECTING DEFECTS

(75) Inventors: Yukihiro Shibata, Fujisawa (JP); Shunji Maeda, Yokohama (JP); Masahiro Watanabe, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 353 days.

(21) Appl. No.: 10/699,934

(22) Filed: Nov. 4, 2003

(65) Prior Publication Data
US 2004/0145734 A1    Jul. 29, 2004

(30) Foreign Application Priority Data
Nov. 6, 2002   (JP)   ............................ 2002-321964

(51) Int. Cl.
*G01N 21/00*   (2006.01)
(52) U.S. Cl. .................................... 356/237.5; 356/369
(58) Field of Classification Search ................ 356/515, 356/450, 512, 237.5, 369; 250/306–311, 250/234–236
See application file for complete search history.

(56) References Cited

U.S. PATENT DOCUMENTS 5,248,876 A * 9/1993 Kerstens et al. ........ 250/559.05
6,690,469 B1 * 2/2004 Shibata et al. ............. 356/369
6,718,082 B2 * 4/2004 Zhao et al. ................... 385/16
2004/0092045 A1 * 5/2004 Bultman et al. .............. 438/16

FOREIGN PATENT DOCUMENTS

JP       9-218165       8/1997

\* cited by examiner

*Primary Examiner*—Gregory J. Toatley, Jr.
*Assistant Examiner*—Tri Ton
(74) *Attorney, Agent, or Firm*—Antonelli, Terry, Stout & Kraus, LLP.

(57) ABSTRACT

Though it is necessary to enhance sensitivity in detecting defects as design rules grow finer, the resolution of a conventional optical system is not sufficient to cope with it. In order to increase vertical resolution, an optical system is so configured to perform detection by differential interference in which beams of light are sheared in two-dimensional directions in a plane perpendicular to an optical axis, thereby achieving zero-order light phase-difference detection. Further, the system is configured such that inconsistencies in brightness caused by thin-film interference, which appear as a noise component in a comparative inspection, are reduced by differential interference and dark-field illumination. Further, with respect to non-critical grains in metal wiring, the contrast of grains is reduced by bright-field/dark-field-combined illumination. The sensitivity in defect detection can be enhanced and highly sensitive inspection can be achieved even when detecting objects of various types and processes.

19 Claims, 16 Drawing Sheets

(Detected amount of light distribution in A-A portion)

(Detected amount of light distribution in A-A portion)

(Detected amount of light distribution in A-A portion)

(Detected amount of light distribution in A-A portion)

FIG.14A
FIG.14B
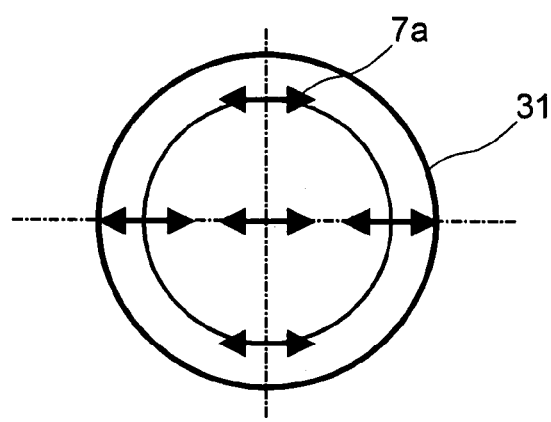
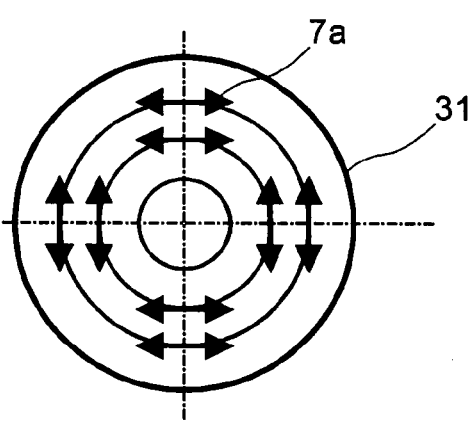

METHOD AND APPARATUS FOR INSPECTING DEFECTS

BACKGROUND OF THE INVENTION

The present invention relates to an optical system of the type used for inspection and observation of defects and foreign substance-induced defects in the surface of a pattern that is formed on a substrate through a thin film preparation process, such as a semiconductor production process and a flat-panel display manufacturing process. The invention also relates to a method of inspecting for defects using the optical system, an apparatus therefor, and a method for effectively using obtained inspection information.

Japanese Patent Laid-Open No. 9-218165 discloses an optical system for inspecting photomasks. This optical system operates as a Mach-Zehnder interferometer in which two sheared beams of light are applied to a mask surface. Then, the two beams that have reflected off the mask are caused to interfere with each other so that an irregularity which constitutes a defect in the mask surface can be detected with a high sensitivity.

In this configuration, the path length of the two sheared optical beam paths becomes long. As a result, a difference between the two branched optical paths can be caused by a disturbance or vibration applied from moving parts. Therefore, the interference intensity of an image plane corresponds to the sum of 1) an optical path difference of the two beams caused by irregularities present on the mask surface, and 2) an optical path difference between the two branched optical paths caused by vibration.

Since the optical path difference between the two branched optical paths caused by vibration fluctuates over time, the interference intensity (brightness of the image) fluctuates over time accordingly. This fluctuation in interference intensity becomes a noise component when detecting defects in the mask surface, so that the defects in the mask surface cannot be detected with a high sensitivity.

Also, the vertical resolution is increased in the shearing direction by applying the two sheared beams of light to an object to be inspected and detecting an interference image. However, the vertical resolution perpendicular to the direction of shearing is not increased. Therefore, the vertical resolution comes to have a directional characteristic, causing such a problem in that the inspection sensitivity varies according to the direction of defects to be inspected.

Further, an object to be inspected may have features produced by a metal wiring process. In metal wiring, fine irregularities called grains are produced in the surface of the object. Since these grains do not affect a device critically, they should not be detected as defects. However, an interference optical system is designed to manifest any irregularity (optical path difference), so that, in the case of a wafer using a metal wiring process, such a manifestation of this type of irregularity by the interference optical system becomes a disadvantage.

It is an object of the present invention to provide an optical system in which optical conditions can be set, such that the contrast of irregularities is kept low in an inspection process where grains exist (example: metal (Al, etc.) wiring process), and irregularities are manifested in a process when grains do not exist. Further, in order to enhance the inspection sensitivity, not only an increase in vertical resolution by an optical system, but also an increase in horizontal resolution is provided.

SUMMARY OF THE INVENTION

The present invention provides a method of inspecting for defects, and an apparatus for implementing the method, comprising an optical system wherein fluctuation in light intensity of light interference over time due to vibration of the optical system and so on, which has not been considered sufficiently in the prior art, is suppressed, and the directional dependence of vertical resolution is reduced.

The present invention also provides a method of inspecting for defects and an apparatus for implementing the method comprising an optical system wherein irregularities in the surface which do not critically affect a device are not detected.

According to the present invention, the polarizing directions of two beams of light that have been sheared by a first birefringent prism are rotated by 45° using a half-wavelength plate. Then, four-beam illumination is applied to an object through a second birefringent prism that is disposed so as to impart shearing in a direction perpendicular to the direction of the former shearing produced by the first birefringent prism. These four beams are provided so as to illuminate the object to be inspected through the same lens to reduce fluctuation of the interference intensity caused by vibration and so on of the optical system. Further, the directional dependence of vertical resolution is decreased by bidirectional shearing intersecting at right angles.

Also, according to the present invention, in the case of an object to be inspected having irregularities that are not critical to a device, the contrast of the irregularities is kept low by bright-and-dark field illumination, and the detection of such irregularities as defects is inhibited.

Further, according to the present invention, the horizontal resolution is increased by controlling the amplitude and phase of a zero-order beam so that the inspection sensitivity is enhanced.

These and other objects, features and advantages of the invention will be apparent from the following more particular description of preferred embodiments of the invention, as illustrated in the accompanying drawings.

BRIEF DESCRIPTION OF THE DRAWINGS

FIGS. 14A and 14B are diagrams which show an example of an electric field vector related to amplitude control of a zero-order light;

DESCRIPTION OF THE PREFERRED EMBODIMENTS

For example, an inspection process in the course of manufacture of semiconductor wafers is roughly classified into inspection of a transistor layer and inspection of a metal wiring layer. In the case of the transistor layer, fine irregularities of a formed pattern can constitute critical defects to a device, and an inspecting apparatus should detect those irregularities as defects. On the other hand, in the case of the metal wiring layer, since irregularities, such as grains, do not critically affect the device, they should not be detected. Accordingly, how irregularities affect a device determines whether the irregularities should be manifested or whether the contrast of them should be kept low. Therefore, in order to carry out an inspection process on semiconductor wafers with a single apparatus, the apparatus must be configured such that an optical condition to manifest irregularities and an optical condition to keep the contrast low can be set individually.

Figure 1:
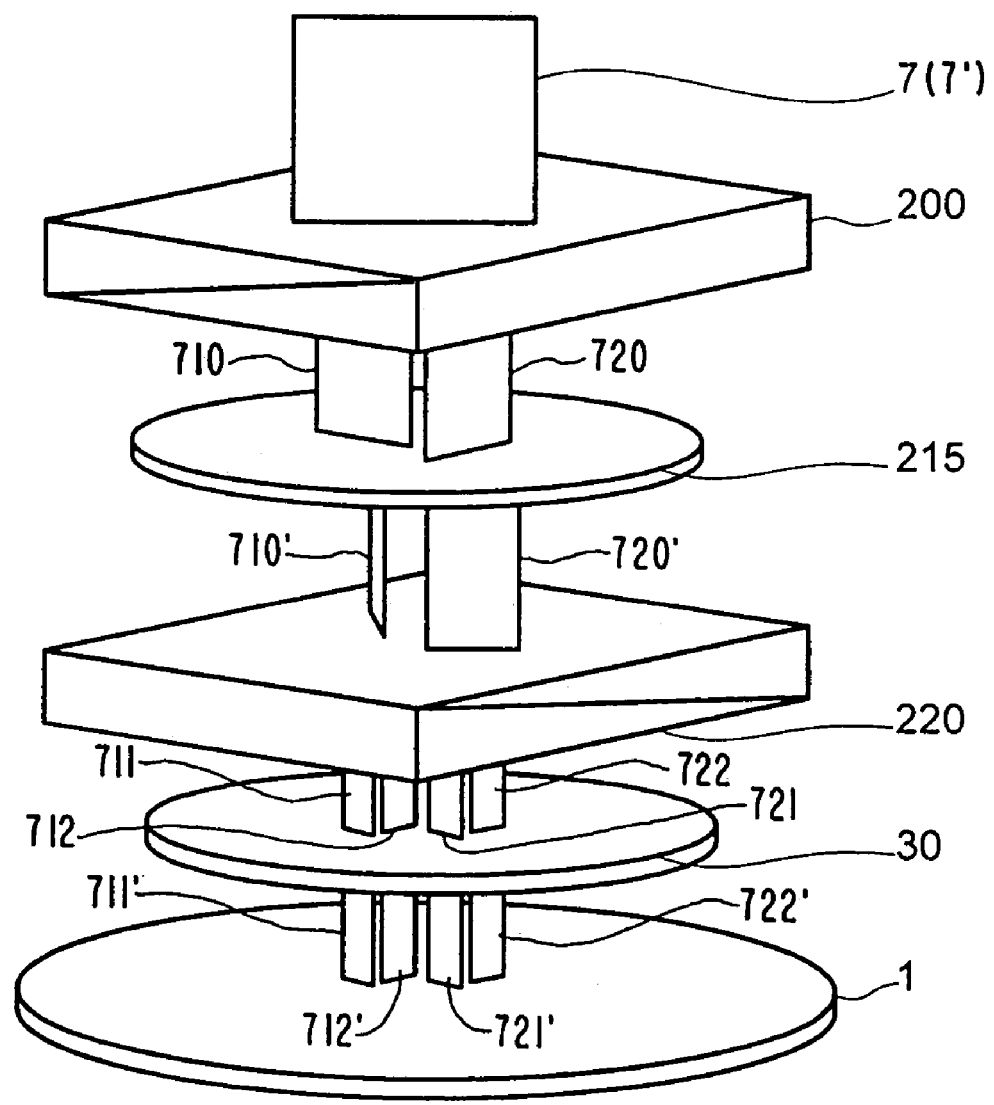
FIG. 1 is a diagram which shows a configuration used to achieve two-dimensional differential interference in a plane perpendicular to an optical axis.

FIG. 1 shows an optical system that is able to manifest irregularities on a wafer 1. Through a birefringent prism 200, incident polarized light 7 for illuminating a wafer is sheared into two beams of light in which the electric field vectors cross at right angles. The direction of the polarized light that has been sheared into two beams 710, 720 is rotated by 45° through a half-wavelength plate 215.

These two beams 710' and 720' of polarized light are further sheared into four beans 711, 712, 721 and 722, crossing at right angles, by a birefringent prism 220, which is disposed to shear the light in a direction perpendicular to that of the birefringent prism 200. These four beams illuminate a wafer 1 through an objective lens 30, and the four reflected four beams 711', 712', 721', 722' are given an optical path difference according to the height of a point where each beam is reflected.

The four reflected beams 711', 712', 721', 722' pass through the objective lens 30, the birefringent prism 220, the half-wavelength plate 215 and the birefringent prism 200, from which the four beams 711', 712', 721' and 722' are brought together as a single beam 7' The combined beams are polarized according to their phase difference. By detecting a particular electric field vector alone, irregularities on a wafer 1 can be manifested.

In order to detect a particular electric field vector, there are devices, such as an analyzer and a polarized beam splitter, which a particular electric field vector can pass through (not shown). With such devices, optical images formed on an image plane can be detected, while the phase difference corresponding to the irregularities of the wafer 1 appear as a brightness.

Figure 2A:
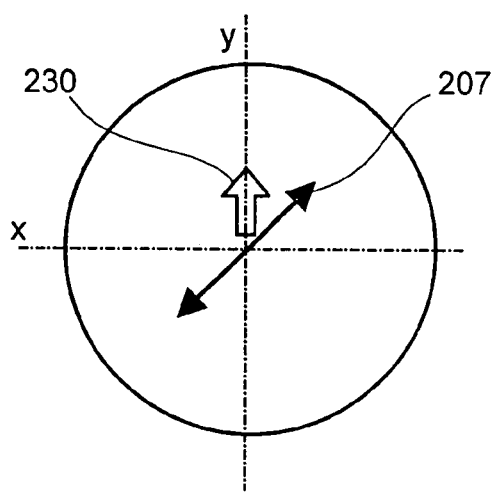
FIGS. 2A to 2D are diagrams which illustrate two-dimensional shearing.
Figure 2B:
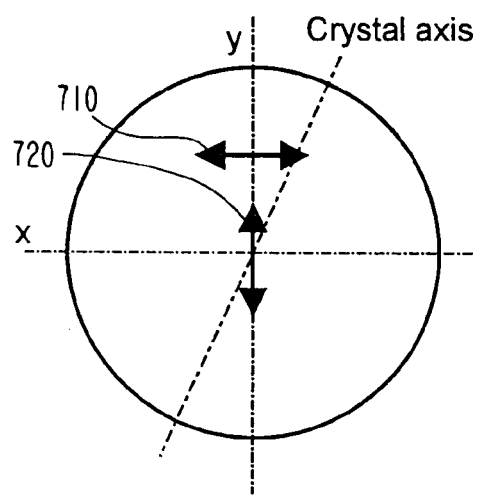

FIGS. 2A to 2D show a polarized state of light passing through each optical element. FIG. 2A shows the shearing direction 230 of the birefringent prism 200 and the direction 207 of incident polarized light. The light passing through the birefringent prism 200 is sheared into two beams 710 and 720 crossing at right angles (FIG. 2B). The directions in which the two beams 710 and 720 vibrate are perpendicular to each other.

Figure 2C:
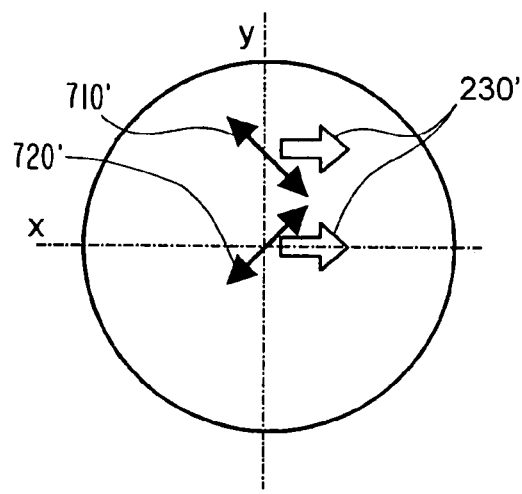
Figure 2D:
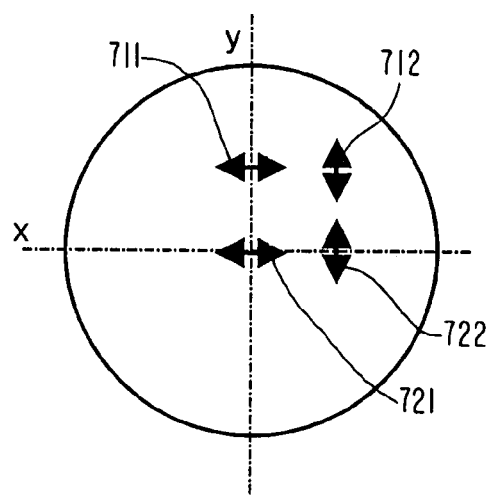

The crystal axis of the half-wavelength plate 215 forms an angle of 22.5° with respect to the shearing direction of the birefringent prism 200. The light passing through the half-wavelength plate 215 becomes-polarized light whose direction of vibration is turned by 45° (FIG. 2C). These two beams 710' and 720' are made to enter a second birefringent prism 220. A shearing direction 230' of the second birefringent prism 220 is set so as to be perpendicular to the shearing direction 230 of the first birefringent prism 200. The light passing through the second birefringent prism 220 is turned into linearly polarized light of four beams 711, 712, 721 and 722, whose shearing directions cross at right angles (FIG. 2D), and the four beams illuminate the wafer 1. The wavefronts of the four beams 711', 712', 721' and 722', reflected off the wafer 1, shift according to the irregularities of the wafer 1.

These beams are combined into a single beam of light 7' by passing through the second birefringent prism 220, the half-wavelength plate 215 and the first birefringent prism 200. The combined beam 7' becomes-polarized according to the wavefronts that the four beams had before being combined. By guiding the directional components of a particular electric field vector through a detection optical path to an optical sensor to form an image, a differential interference system is established in which irregularities of two directions, crossing at right angles on a wafer surface, can be detected with a high resolution.

Figure 3A:
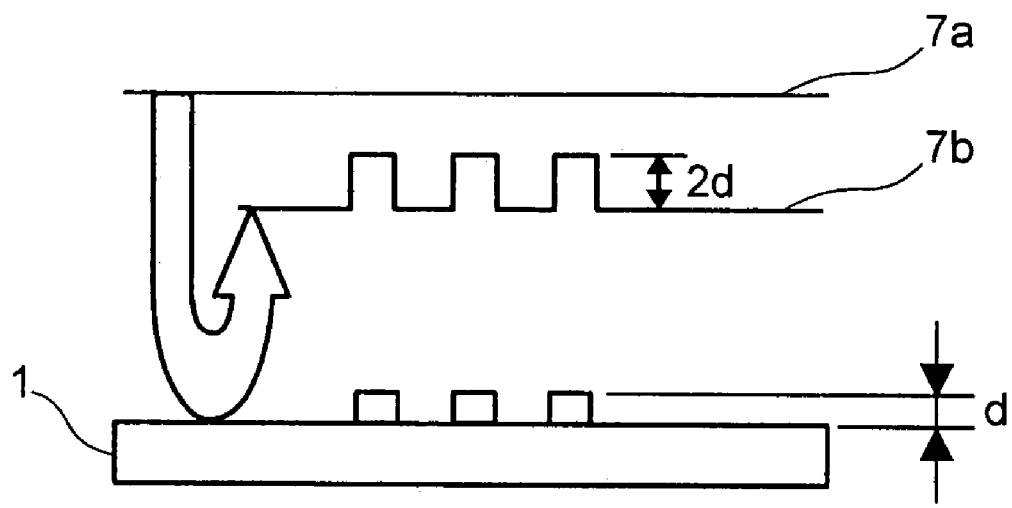
FIGS. 3A and 3B are diagrams which illustrate differential interference.
Figure 3B:
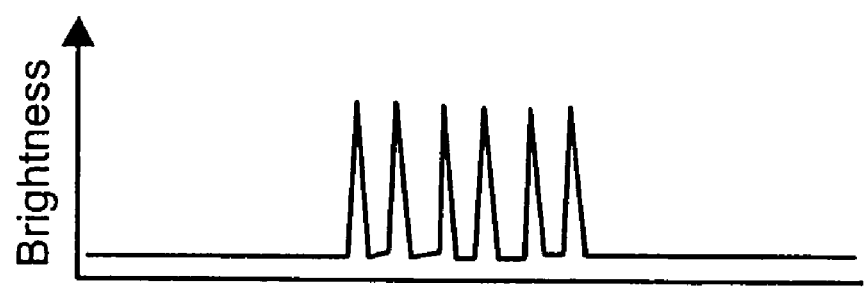

FIGS. 3A and 3B illustrate the principle of differential interference. One of the sheared beams is referred to as a beam 7a. This illuminating beam is a plane wave which has a phase of the same level, and according to the difference in level d of the surface of the wafer 1, the phase of the wavefront of the reflected light 7b varies by 2d. Through the interference of this plane wave and another sheared plane wave, it is possible to detect an edge portion of a pattern brightly. Further, in order to detect the edge portion of the pattern in a brightened state and the flat portion in a darkened state, it is preferable that the beam of light entering the birefringent prism 200 is linearly polarized and the direction in which the incident polarized light vibrates forms an angle of 45° with respect to the direction of shearing. This is because it is desirable for the amplitudes of the two sheared beams to be almost the same.

Figure 4:
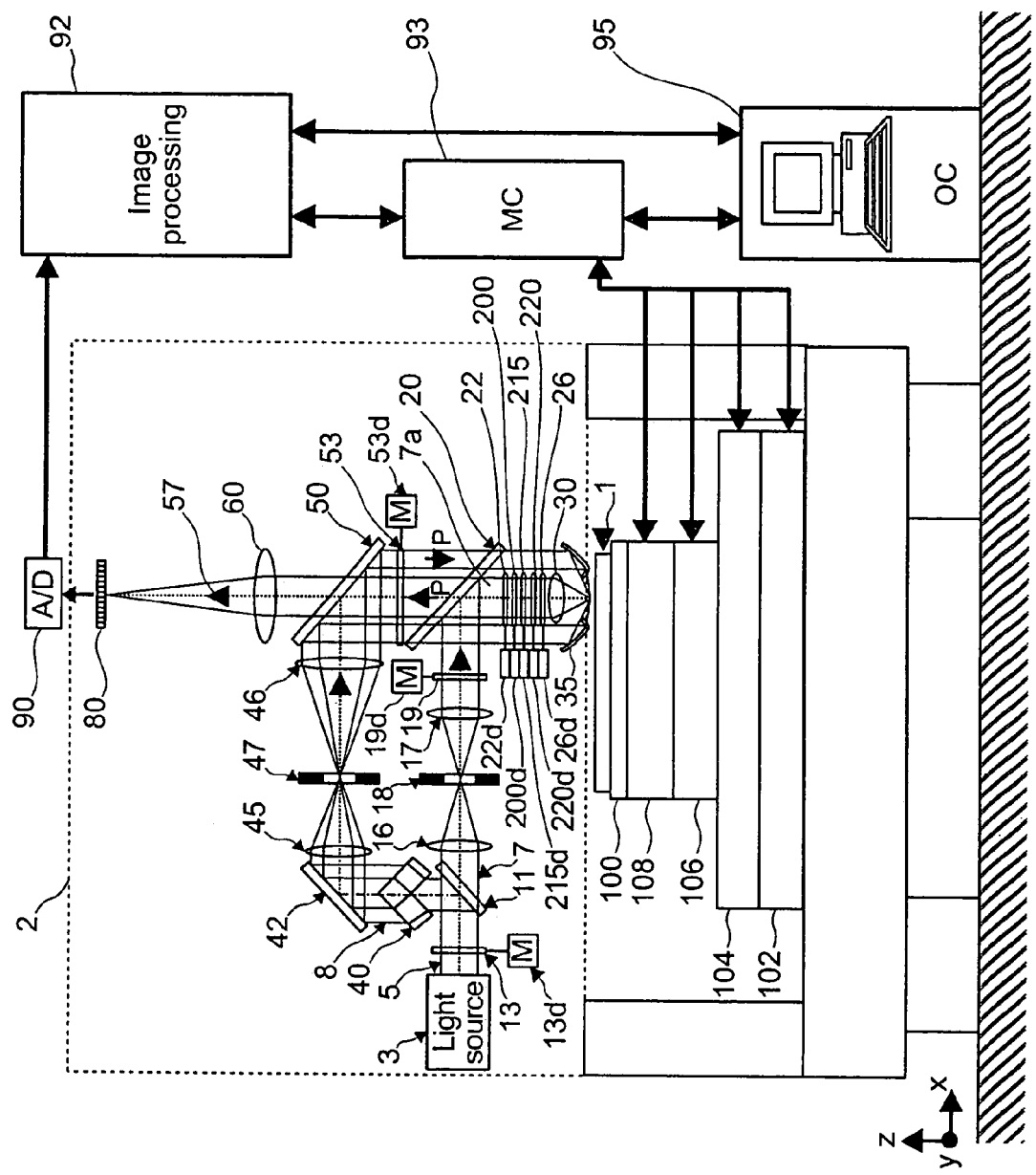
FIG. 4 is a schematic diagram showing the configuration of an embodiment of the present invention.

FIG. 4 shows the basic configuration of an inspection apparatus according to the present invention. This embodiment includes a bright-field illumination function and a dark-field illumination function wherein differential interference is available. According to the configuration shown in FIG. 4, a beam of light leaving a light source 3 (laser or a light source lamp) enters a half-wavelength plate 13. The half-wavelength plate 13 is configured such that an angle formed by a crystal axis with respect to a direction in which the incident polarized light vibrates is optionally controllable by a rotary mechanism 13d about an optical axis. Further, the rotary mechanism associated with various optical parts are indicated in the drawing by appending 'd' to a numeral which identifies the optical part (for example, 13d').

The beam of light 7 passing through the half-wavelength plate 13 enters the PBS (Polarizing Beam splitter) 11, and it is divided into two optical paths by a branching ratio of polarization corresponding to the PBS surface. The beam of light passing through the PBS 11 enters a half-wavelength plate 19 after its beam diameter has been adjusted by a lens 16, an aperture diaphragm 18 and a lens 17. An s-polarized component alone of the light passing through the half-wavelength plate 19 is reflected toward a wafer by a PBS 20, and it becomes bright-field illumination light which illuminates the wafer 1 through an objective lens 30. Also, it is possible to change the polarizing direction (electric field vector) of the light entering the PBS 20 by rotating the half-wavelength plate 19 using the rotary mechanism 19d. Thus, the amount of light of the bright-field illumination can be continuously controlled.

Further, the light reflected off the PBS 11 becomes a ring-shaped (zonal) hollow beam 8 after passing through a meniscus cone lens 40, and the diameter of the ring is adjusted by lenses 45 and 46 and aperture diaphragm 47 after being reflected by mirror 42. The s-polarized component of this light is reflected toward the wafer 1 by a PBS 50, and it is rotated and polarized as p-polarization with respect to the PBS 20 by the half-wavelength plate 53, which can be rotated by the rotary mechanism 53d. This light passes through the PBS 20, reaches the mirror 35 by way of an annular path passing outside the objective lens 30, and it is reflected off the mirror 35 to become dark-field illumination light that illuminates the wafer 1 obliquely from outside of the objective lens 30. The amount of light of this dark-field illumination can be continuously controlled by adjusting the polarizing direction in which the light enters the PBS 20 by way of the half-wavelength plate 53.

Among the light scattered/diffracted on the wafer 1 by the dark-field illumination, the beams of light passing through an NA (Numerical Aperture) of the objective lens 30 pass a quarter-wavelength plate 26, a birefringent prism 220, a half-wavelength plate 215, a birefringent prism 200, and a half-wavelength plate 22, and components of the p-polarized light are guided into a detection optical path 57 with respect to the PBS 20. These beams of light pass through the PBS 50 and form an image of the wafer 1 on an image sensor 80 by way of an image-formation lens 60. Further, rotary mechanisms 26d, 220d, 215d, 200d, and 22d for adjustment about the optical axis are provided respectively to the quarter-wavelength plate 26, the birefringent prism 220, the half-wavelength plate 215, the birefringent prism 200, and the half-wavelength plate 22. Also, in the case of the bright-field illumination, among the light reflected/diffracted/scattered on the wafer 1, the beams of light entering the NA of the objective lens 30 pass along the same optical path as the case of the dark-field detection light and form an image of the wafer 1 on the image sensor 80.

The light intensity distribution detected by the image sensor 80 is photo-electrically converted and is inputted to an A/D converter 90 as an analogue signal. Image data converted into digital signals are sent to an image processor 92, and the defects are detected by a comparative test and so on. This defect information is sent to an OC (Operating Computer) 95 so that the defect coordinates and their feature amount can be referred to. Further, when the image sensor 80 is of a TDI (Time Delay Integration) type, it is necessary to obtain an image while moving the wafer 1 at a constant speed. In this case, it is desirable to synchronize the movement of the wafer 1 and the vertical transmission of the TDI. In such a case, information that the wafer 1 is being moved is obtained by an MC (Mechanical Controller) 93 and the timing for the vertical transmission of the TDI is controlled.

The wafer 1 is mounted on a Y stage 102 and an X stage 104 to enable it to be moved in a horizontal plane. There is also provided a θ stage 106 for positioning the wafer 1 in parallel with the direction in which the stages are moved at a constant speed, and a Z stage 108 for positioning the objective lens in the direction of the optical axis. Mounted on these stages is a wafer chuck 100 in which the wafer 1 is held. The positions of the Y stage 102, X stage 104, and θ stage 106 are measured by a linear scale or a laser dimension measurement machine (not shown). The moving information (positional information) concerning movement of the wafer 1 may be obtained by the linear scale or the laser dimension measurement machine.

Figure 5:
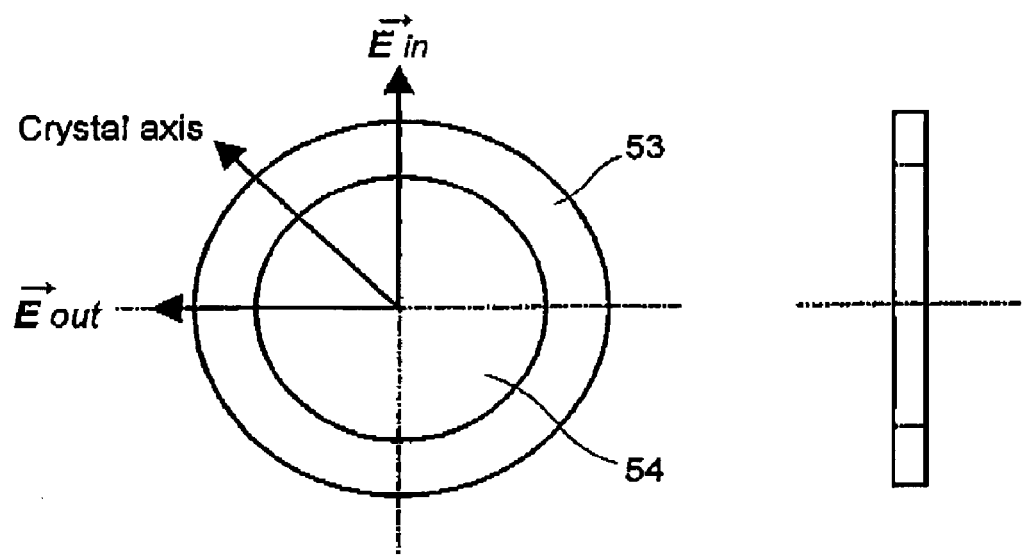
FIG. 5 is a diagram showing the outward appearance of a half-wavelength plate for dark-field illumination.

The configuration of a half-wavelength plate 53 that is disposed (Z stage 108) in the dark-field illumination path is shown in FIG. 5. A birefringent phase difference material (for example, crystal, magnesium fluoride, etc.) is disposed in a (zonal) region of the half-wavelength plate 53 where the light of dark-field illumination passes through. Assume that the angle formed by the crystal axis of the half-wavelength plate 53 and the electric field vector Ein of the incident linearly polarized light is set to 45°. In this case, an electric field vector Eout of the linearly polarized light passing through the half-wavelength plate 53 forms an angle of 90° (direction to catch the crystal axis) with the Ein. Further, the central portion 54 where the light of dark-field illumination does not pass through is hollow. Therefore, by adjusting the angle formed by the half-wavelength plate 53 and the incident electric field vector Ein, the amount of light of the dark-field illumination passing through the PBS 20 can be controlled.

Further, to adjust the distribution of the amount of light of the bright-field illumination and the dark-field illumination, the angle formed by the crystal axis of the half-wavelength plate 13 of FIG. 4 and the vibration direction of the linearly polarized light entering the half-wavelength plate 13 can be adjusted, which makes it possible to adjust the branching ratio of the PBS 11.

Figure 6:
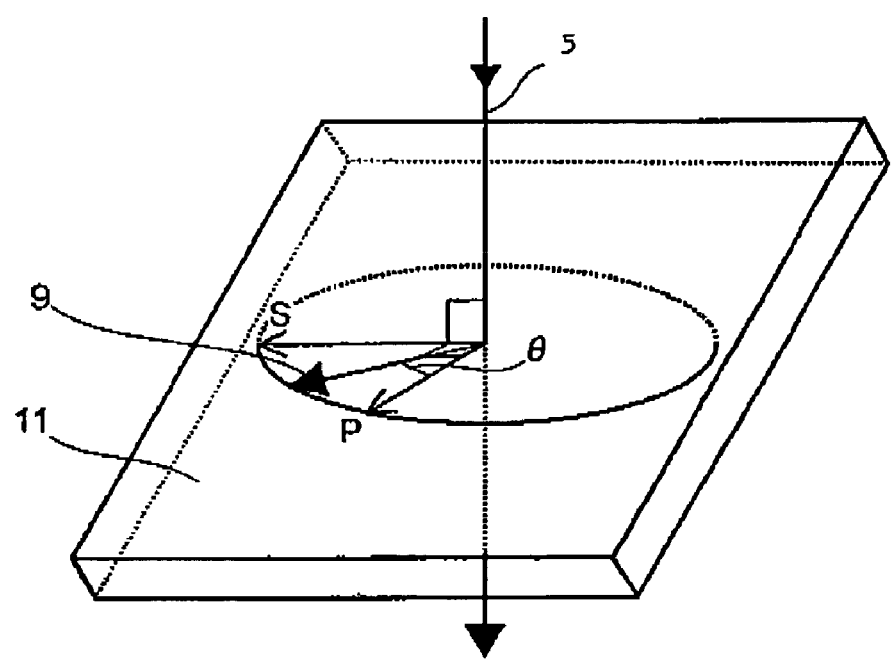
FIG. 6 is a diagram which illustrates a polarized beam entering a PBS (Polarized Beam Splitter)
Figure 7:
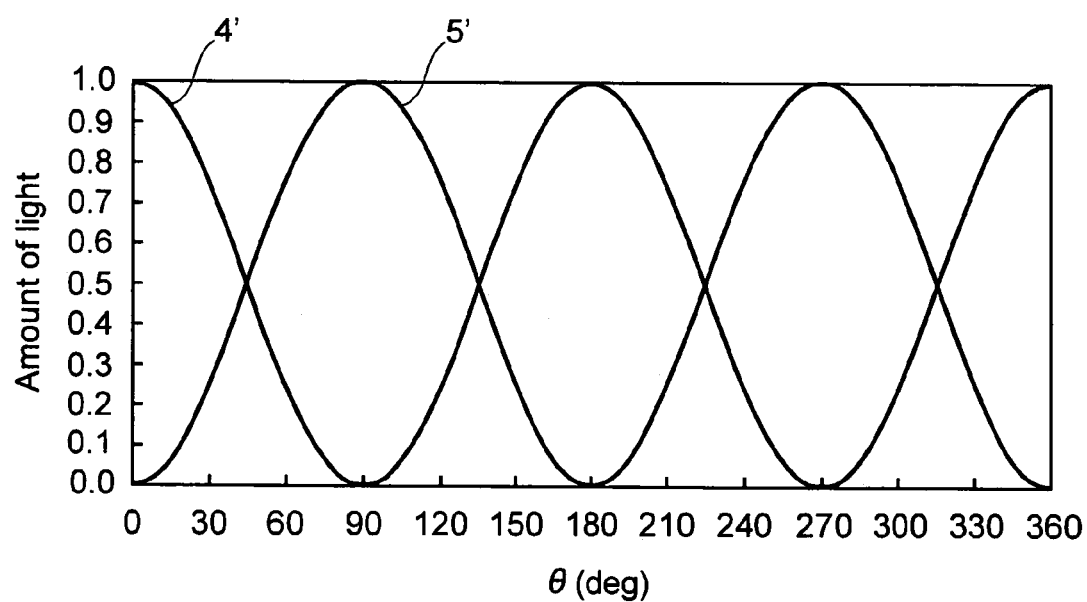
FIG. 7 is a diagram which shows an outline of the distribution of the amount of light in bright-field illumination and dark-field illumination.

FIG. 6 shows the relation between linearly polarized light 5 entering the PBS 11 and the direction of the incident polarized light (s-, p-polarization). The angle formed by the direction of p-polarization and the vibration direction 9 of the incident linearly polarized light 5 is referred to as θ. FIG. 7 shows the relation between the amount of bright-field and dark-field illumination and the angle θ. When θ=0°, the light entering the PBS becomes p-polarized and all the light passes through.

In the configuration shown In FIG. 4, the transmitted light heads for the side of the bright-field illumination 7. Therefore, there is no light heading for the side of the dark-field illumination 8. When θ is increased, the light heading for the side of the bright-field illumination 7 propagates while following a cosine curve 5', and the light heading for the side of the dark-field illumination 8 propagates while following a sine curve 4' as seen in FIG. 7. Therefore, by adjusting θ, the distribution of the amount of the light heading for the side of the bright-field illumination 7 and the light heading for the side of the dark-field illumination 8 can be adjusted. Thus, the balance of illumination of the dark-field and the bright-field can be adjusted, which can achieve a highly sensitive inspection.

FIGS. 8A to 8F an effect of the improvement in inspection sensitivity which can be achieved by differential interference. Dies 200 are arranged systematically on the wafer 1. Identical patterns are formed in each die, and defects are detected by a comparative inspection. The comparative inspection is an inspection, for example, in which images of the identical pattern portions of a die 200a and a die 200b are aligned to seek a difference in density between digital images. Then, a portion whose difference in density exceeds a specified threshold value is detected as a defect.

However, there is an electric insulating film (for example, SiO2) formed on the wafer 1. This SiO2 film is optically transparent. Therefore, it causes so-called thin film interference, which is interference between the light reflected off an upper surface of the film and the light reflected off an under surface of the film.

Figure 8A:
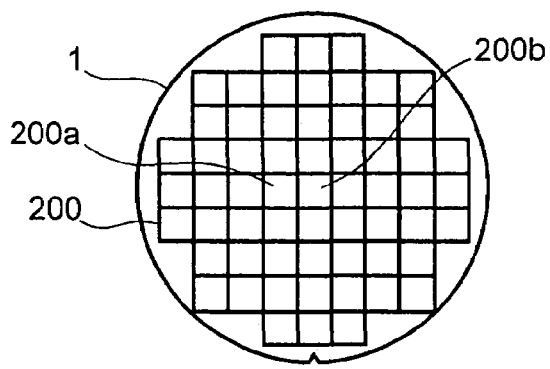
FIGS. 8A to 8F are diagrams and graphs which illustrate an effect of a dark-field inspection when used to inhibit inconsistencies in brightness.
Figure 8B:
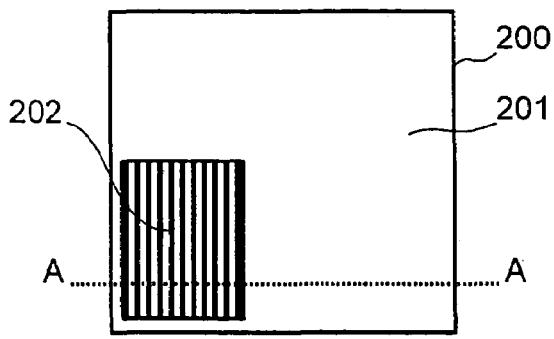
Figure 8C:
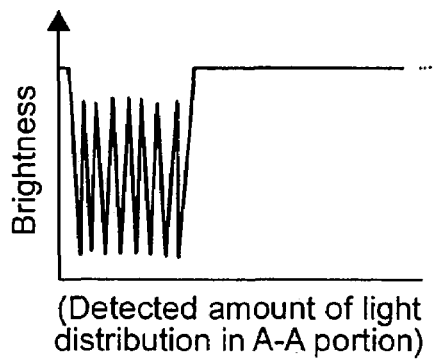
Figure 8D:
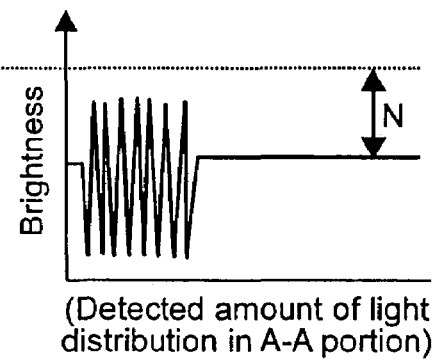

FIG. 8B shows an enlarged view of the die 200. A pattern 202 is formed in the die, and the rest of the region 201 is covered with SiO2. Assume that there is a difference in film thickness between SiO2 films of the die 200a and the adjacent die 200b. In this case, with respect to the brightness distribution of the digital image in the A-A portion during the bright-field detection, there is a difference of N value in brightness of flat portions between distribution (FIG. 8C) of the die 200a and distribution (FIG. 8D) of the die 200b. Therefore, the threshold value has to be greater than the value N.

Figure 8E:
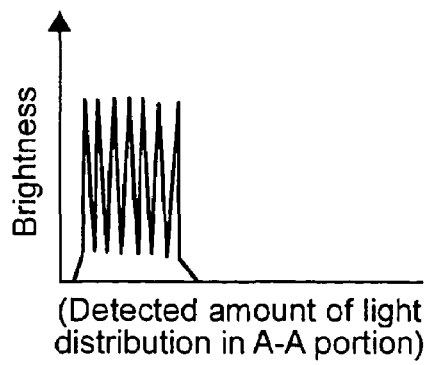
Figure 8F:
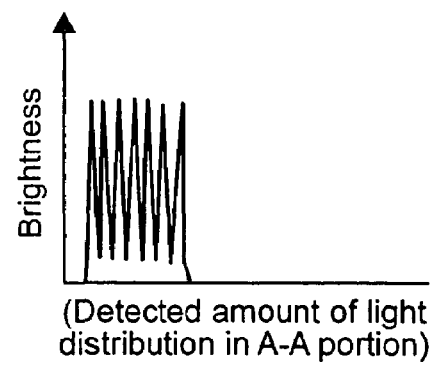

On the contrary, with respect to images of differential interference (the case of die 200a is shown in FIG. 8E and the case of die 200b is shown in FIG. 8F), flat portions can be detected in a darkened state. Therefore, it becomes possible to reduce inconsistencies in brightness caused by unevenness in the film thickness of the SiO2. Therefore, it becomes possible to set the threshold value to a small value and to enhance the inspection sensitivity compared with bright-field detection. Further, this effect can be achieved by detecting the flat portion in a darkened state. As another method, it is possible to detect the flat portion in a darkened state by dark-field detection, which brings about the same effect.

Figure 9A:
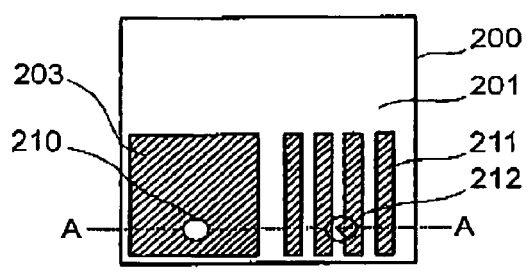
FIGS. 9A to 9D are diagrams and graphs which illustrate an effect of bright-and-dark field illumination.
Figure 9B:
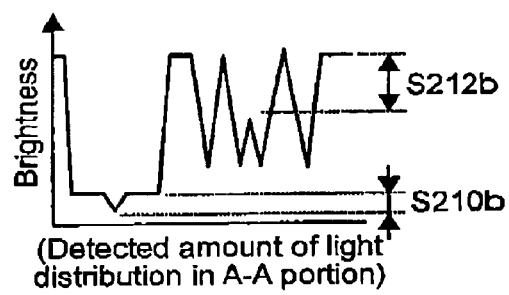

An effect achieved by bright-field illumination will be explained with reference to FIGS. 9A to 9D. Assume that, in FIG. 9A, a pattern 203 having a low reflective surface and a linear pattern (Line & Space; hereafter called "L & S") 211 are formed in the die 200. Also, assume that the rest of the region is coated with an SiO2 film. Further, this die has a defect 210 whose reflectance is lower than that of the pattern 203 and a massive defect 212 of the L & S portion. FIG. 9B shows the amount of light distribution of the bright-field detection in the A-A portion of the die.

In the bright-field detection, a signal level S210b of the dark defect 210 on the pattern 203 having a low reflectance is low and it is hard to detect such a defect. On the other hand, the massive defect having a low reflectance is formed against a bright background. Therefore, the difference S212b in density gets comparatively greater and it is easy to detect such a defect. Namely, when there is a great difference in brightness between the background and the defective portion, it is easy to detect the defect.

Figure 9C:
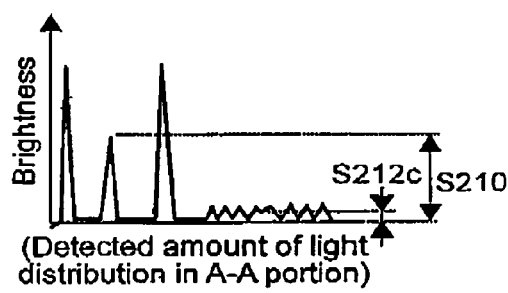

FIG. 9C shows the amount of light distribution of the dark-field detection in the A-A portion. In the dark-field detection, irregularities on the wafer 1 can be detected as a brightness. Therefore, it is possible to detect convex defects having a lower reflectance on the pattern having a low reflectance with a high signal level S210c. On the contrary, since the horizontal resolution of the dark-field illumination is optically low, the signal level S210c of massive defects becomes low. Thus, the method which is able to detect the defect 210 easily is the dark-field detection method, and the method which is able to detect the defect 212 easily is the bright-field detection method.

Figure 9D:
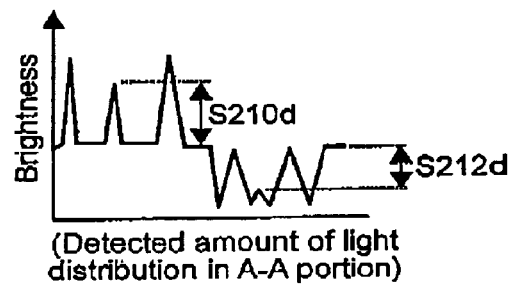

Accordingly, a detection method in which signal levels of both the defects are raised on the average to make the detection of respective defects easier employs the bright-and dark-field illumination. This is a combination of the bright-field illumination and the dark-field illumination. FIG. 9D shows the amount of light distribution in the A-A portion in the case where both bright-field and dark-field illumination are employed.

Signal levels S210d and S212d of the defect 210 and the massive defect 212 become average values of the signal levels of the bright-field illumination and the dark-field illumination. With the bright-field illumination, the inspection sensitivity can be enhanced on the average. Further, by adjusting the amount of light balance of the bright-field illumination and the dark-field illumination, the amount of light balance of illumination needed to enhance the inspection sensitivity with respect to various patterns can be achieved.

Figure 10:
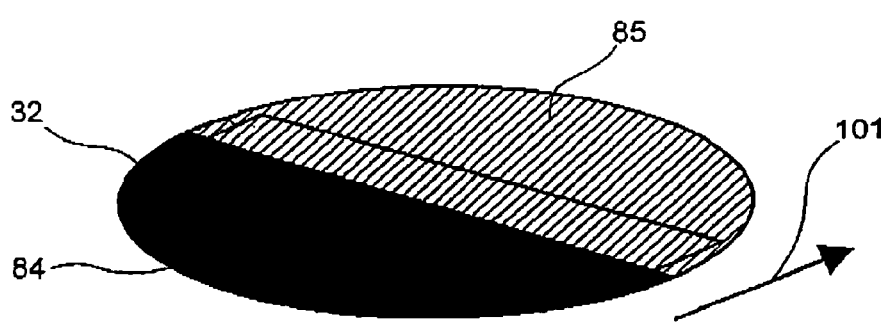
FIG. 10 is a diagram which separate illumination of the bright-and dark-field.

A method to adjust the illumination areas of the bright-field illumination and dark-field illumination will be explained with reference to FIG. 10. There are aperture diaphragms (a bright-field aperture diaphragm 18 and a dark-field aperture diaphragm 47 in FIG. 4) provided respectively in the bright-field illumination path and the dark-field illumination path. For example, through these diaphragms, a half 84 of the field 32 is bright-illuminated and the other half 85 is dark-illuminated. Further, the image sensor 80 is of the TDI type and is so disposed that the bright-field illuminating light and the dark-field illuminating light are added together in the direction 101 of the vertical transmission.

Figure 11:
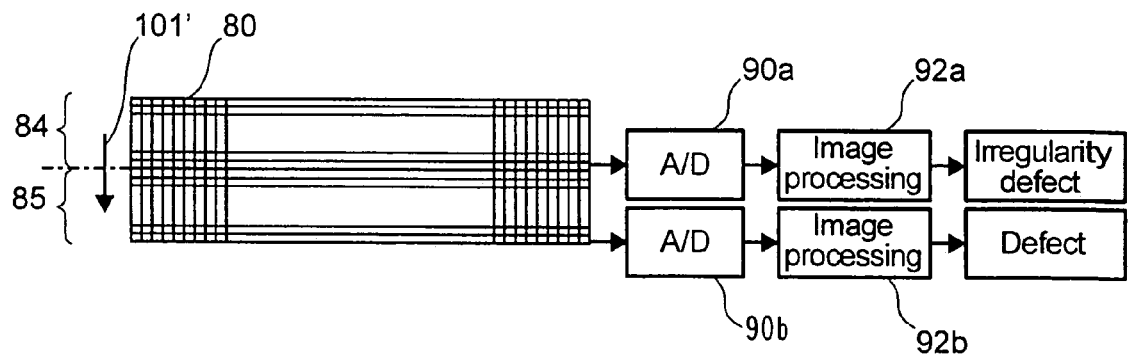
FIG. 11 is a diagram which shows an example of a separate detection of bright-and dark-field illuminated image.

FIG. 11 shows a method which may be employed to individually detect images in the bright-field illumination and dark-field illumination by use of a single image sensor 80. Outputs are made in a parallel manner with respect to a region of a CCD (Charge Coupled Device) making up the TDI image sensor 80 applicable to the bright-illuminated region 84 and the dark-illuminated region 85. Further, the numeral 101' indicates the vertical transmitting direction by the TDI. Analog image data outputted in parallel is converted into digital images by respective A/D converters 90a, 90b, and defects are detected by image processors 92a, 92b.

Defects detected in each manner have characteristic shapes according to their respective illumination method. For example, defects detected in the dark-field detection have irregularities in the direction of the optical axis. Therefore, these defects can be classified optically, for example, like irregularity defects, such as foreign substances which are defects detected by the dark-field illumination. Thus, in the case where large amounts of defects are detected, when observing them, it becomes possible to selectively review a desired defect.

Accordingly, it is possible to achieve early detection of an abnormality in a process of manufacturing semiconductors or dust from semiconductor manufacturing equipment. Thus, the yield in the manufacture of semiconductor devices can be maintained at a high level. Further, a method can naturally be conceived in which, unlike the case shown in FIG. 10, the region is not divided into a bright-field illumination region and a dark-field illumination region, but where bright-field and dark-field illumination are applied in an overlapping manner.

Figure 12A:
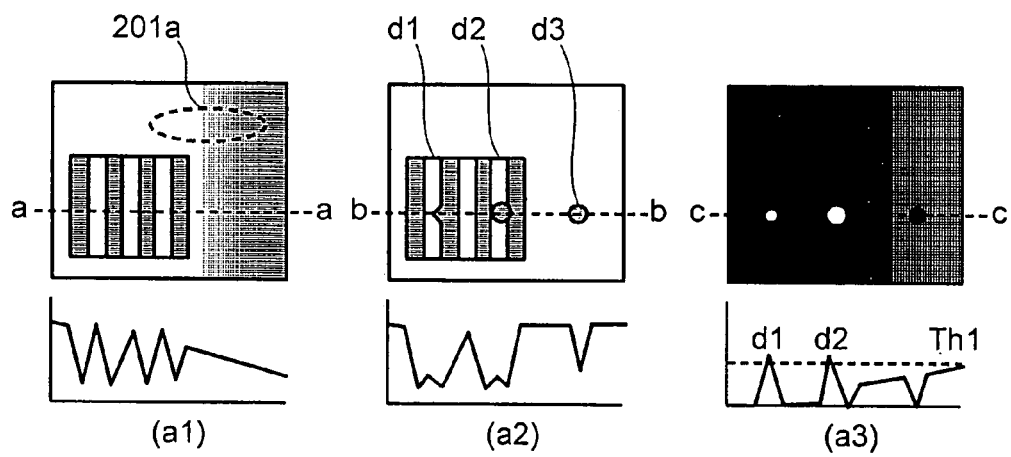
FIGS. 12A and 12B are diagrams which show an example of the effects produced by dark-field illumination.

FIG. 12A shows an image detected by bright-field detection when there is an unevenness in the film thickness of an SiO2 film. Images of neighboring dies are shown in diagrams (a1) and (a2). With respect to the one shown in diagram (a1), the SiO2 film has an unevenness in the film thickness, and there is a reflectance distribution (inconsistencies in brightness) shown in 201*a*. On the contrary, there are three kinds of defects d1, d2, and d3 in diagram (a2). The amount of light distribution of the same coordinates of the a-a portion and b-b portion design-wise for diagrams (a1) and (a2) will be shown respectively.

Further, the difference in the images of diagrams (a1) and (a2) is shown in diagram (a3). In order to not detect inconsistencies in brightness caused by unevenness in the film thickness of SiO2 as defects, the threshold value has to be set to Th1. When the threshold value is set to Th1, defects d1 and d2 can be detected, but defect d3 cannot be detected. In particular, defect d3 is a darkened defect in a bright field. Since the brightness of the adjacent die used for comparison is darkened by the influence of the thin-film interference, the absolute value of the difference between inconsistencies in brightness has become small.

Figure 12B:
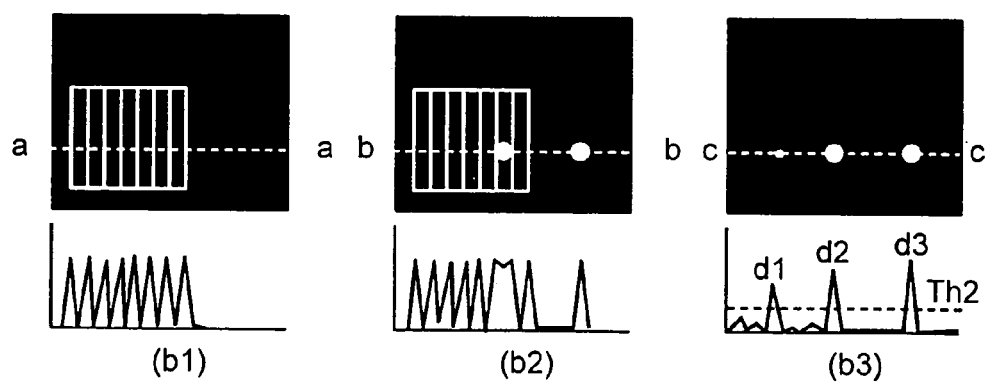

On the other hand, an image of the dark-field illumination is shown in FIG. 12B. In this case, since inconsistencies in brightness can be reduced, the threshold value has been set to a small value. Thus, it becomes possible to detect all three kinds of defects.

Figure 13A:
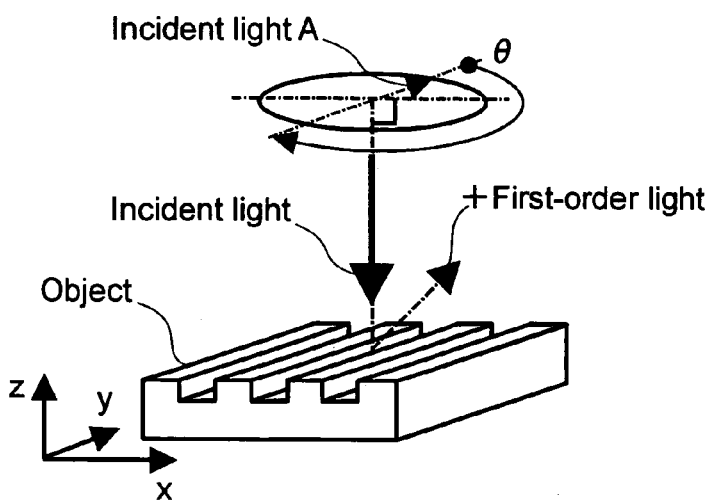
FIGS. 13A to 13C are a diagram and graphs which show an example related to amplitude control of a zero-order light.
Figure 13B:
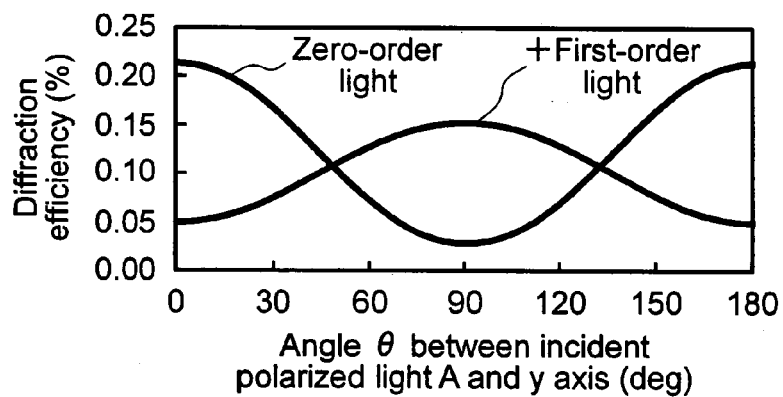
Figure 13C:
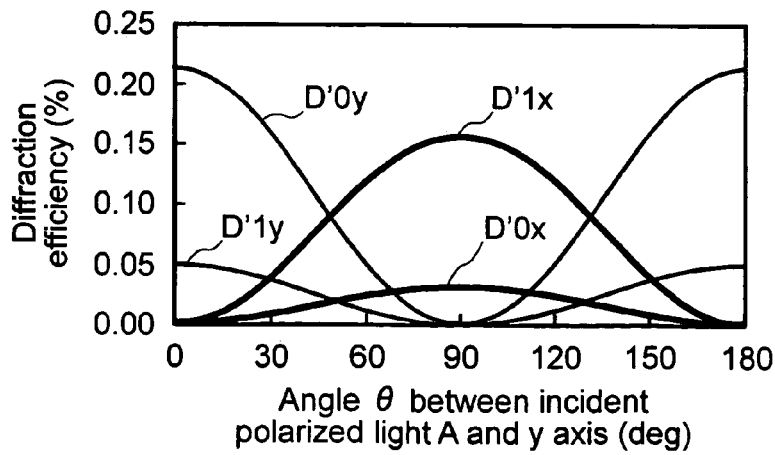

FIGS. 13A to 13C show a method which may be employed to increase the horizontal resolution of an optical system (the resolution in a plane perpendicular to an optical axis of an objective lens). Assume that a Line & Space pattern parallel to the y axis is formed on a surface of the wafer 1 to be inspected, as seen in FIG. 13A, Also, assume that the wafer 1 is illuminated vertically by linearly polarized light. Further, assume that the angle formed by the y axis and the direction in which an electric field vector of the linearly polarized light A is projected in an x-y plane is θ1. An example of the diffraction efficiency in this case is shown in FIG. 13B.

According to the illustrated example, when the incident polarized light A and they y axis are in parallel, the intensity of zero-order light is strong, and when they cross at right angles, the intensity of first-order light is strong. An optical image formed on an image plane is produced by interference of the zero-order light and the first-order light. Therefore, it is desirable that, for a higher image contrast, the amplitude of the zero-order light and that of the first-order light are equal to each other.

However, when a pattern formed on the wafer 1 is finer, the diffraction angle becomes greater, and the ratio of higher-order diffracted light transmitted into the NA of an objective lens becomes low. Therefore, the amplitude with which the higher-order diffracted light reaches the image surface gets smaller and the contrast of the optical image is lowered.

A method of enhancing the image contrast of this fine pattern will be described. For example, when the angle formed by the incident polarized light A and the y axis is set to around 50°, the diffraction efficiency of the zero-order light and the first-order light becomes about 0.11. A graph is shown in FIG. 13C in which an electric field vector of the zero-order light and the higher-order diffracted light reflected through an objective lens is projected to an x-y plane and decomposed into x-y directions (it is approximated that the light reflected through the objective lens is parallel to the optical axis).

Assume that a component of the zero-order light in the x-direction is D' Ox, a component of the same in the y-direction is D'0y, a component of the first-order light in the x-direction is D'1x, and a component of the same in the y-direction is D'1y. In this case, where the angle formed by the incident polarized light A and the y axis is about 50°, the components D'0y and D'1x have a diffraction efficiency of about 0.09. Therefore, by placing an analyzer to detect only such electric field vectors that form an angle of 45° with the x-direction and the y-direction, the directions in which the zero-order light and the first-order light vibrate can be parallel to each other and their amplitudes can be almost the same. In this manner, optical images having a higher contrast can be obtained.

With respect to a direction 7*a* in which the light linearly polarized by the PBS vibrates, a cross section 31 (an x-y plane) perpendicular to an optical axis is shown in FIG. 14A. The direction in which the linearly polarized light vibrates is aligned in parallel with the x axis. On the contrary, in order to detect patterns formed on a wafer in various directions with a high contrast, it is necessary to have polarized light vibrate in the tangential direction of concentric circles about the optical axis, as seen in FIG. 14B. An embodiment for achieving this will be described with reference to FIGS. 15A to 15C.

Figure 15A:
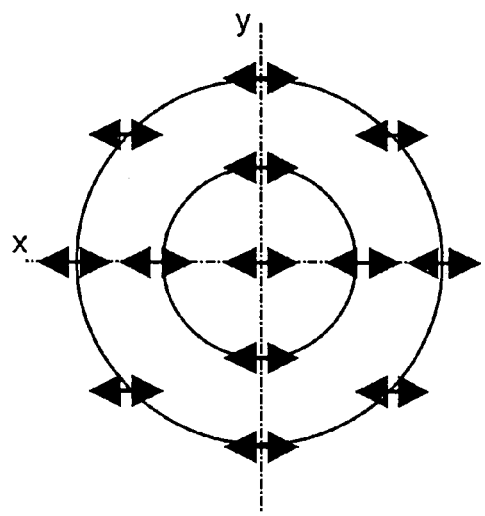
FIGS. 15A to 15C are diagrams which show an example of isotropic illumination by polarized light.
Figure 15B:
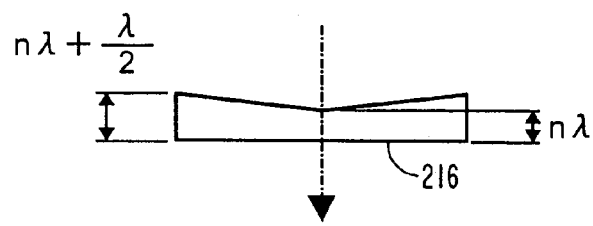
Figure 15C:
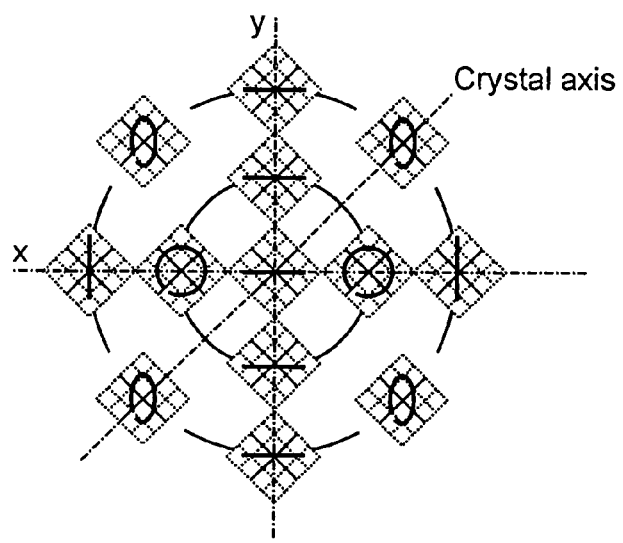

The direction in which the light reflected off the PBS 20 vibrates is shown in FIG. 15A. In the drawing, the light is linearly polarized light which vibrates in a direction parallel to the x axis. This linearly polarized light is allowed to enter a birefringent wavelength plate 216 whose thickness is modified to have a V-shape, as seen in FIG. 15B. The thickness of this birefringent wavelength plate is formed such that there is a difference in birefringent phase of nλ+λ/2 around the periphery; and, at the central portion, there is a difference in birefringent phase of nλ. The crystal axis of the wavelength plate is set at an angle of 45° with respect to the x axis. Thus, the direction of vibration of the light passing through the wavelength plate is rotated by 90° at both ends on the x axis with respect to the direction of the polarized light before entering the wavelength plate, as seen in FIG. 15C. Further, at positions other than the both ends, they turn to be elliptically polarized light.

In this way, with respect to the polarized light, before passing through the wavelength plate, there are more tangential components of concentric circles about the optical axis, which makes it possible to detect patterns comparatively in various directions with a higher contrast.

Figure 16A:
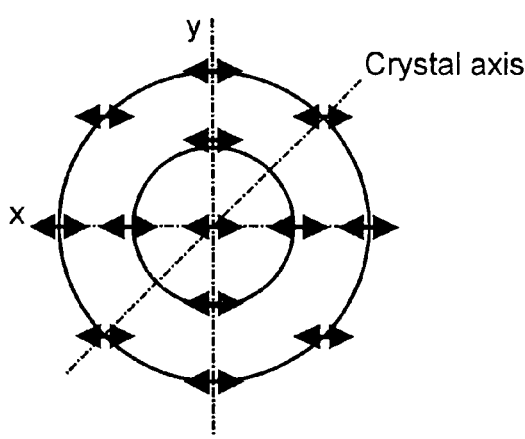
FIGS. 16A to 16E are diagrams which show an example of isotropic illumination by polarized light.
Figure 16B:
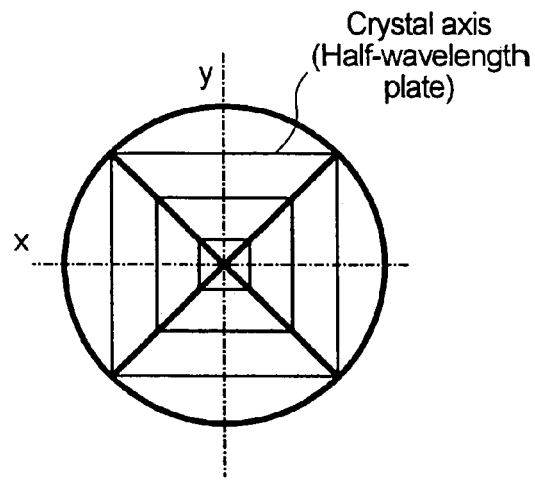
Figure 16C:
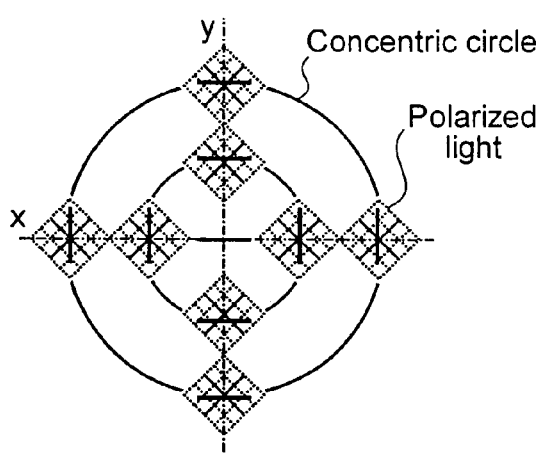
Figure 16D:
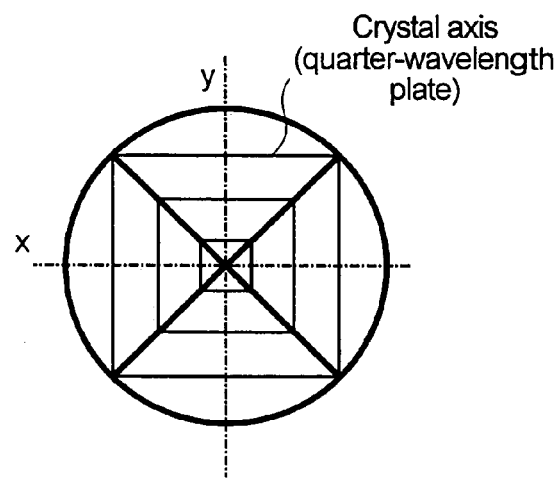
Figure 16E:
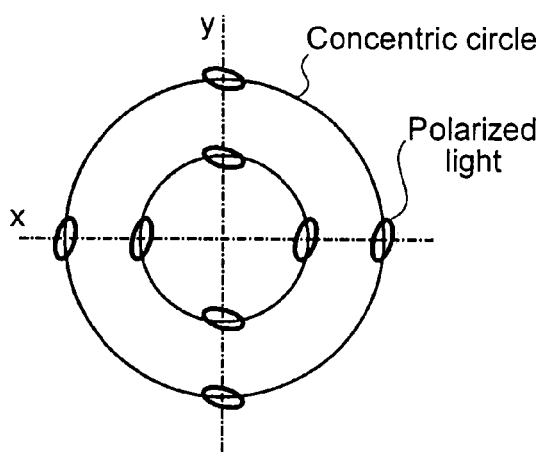

As another embodiment, FIGS. 16A to 16E show a method which calls for bonding wavelength plates together. The direction in which the light linearly polarized by the PBS 20 vibrates is shown in FIG. 16A. The direction in which the light vibrates is parallel to the x axis. In such an arrangement, a half-wavelength plate is formed of four plates which are bonded together in a direction such that the crystal axes (lagging phase axes) of adjacent wavelength plates cross at right angles, as seen in FIG. 16B. The linearly polarized light passing thorough the wavelength plate is, as shown in FIG. 16C, tangential to concentric circles about the optical axis. This linearly polarized light is allowed to enter a quarter-wavelength plate that is similarly formed by bonding four quarter-wavelength plates arranged adjacent to each other so that the crystal axis (lagging phase axis) of adjacent plates cross at right angles, as seen in FIG. 16D. By arranging the crystal axis of the bonded quarter-wavelength plate and the direction in which the incident polarized light vibrates to form an angle θ1, the ellipticity of the transmitted polarized light becomes tan θ1, as seen in FIG. 16E. Accordingly, with respect to patterns that are perpendicular to each other, respective highly contrasted images can be detected.

Figure 17:
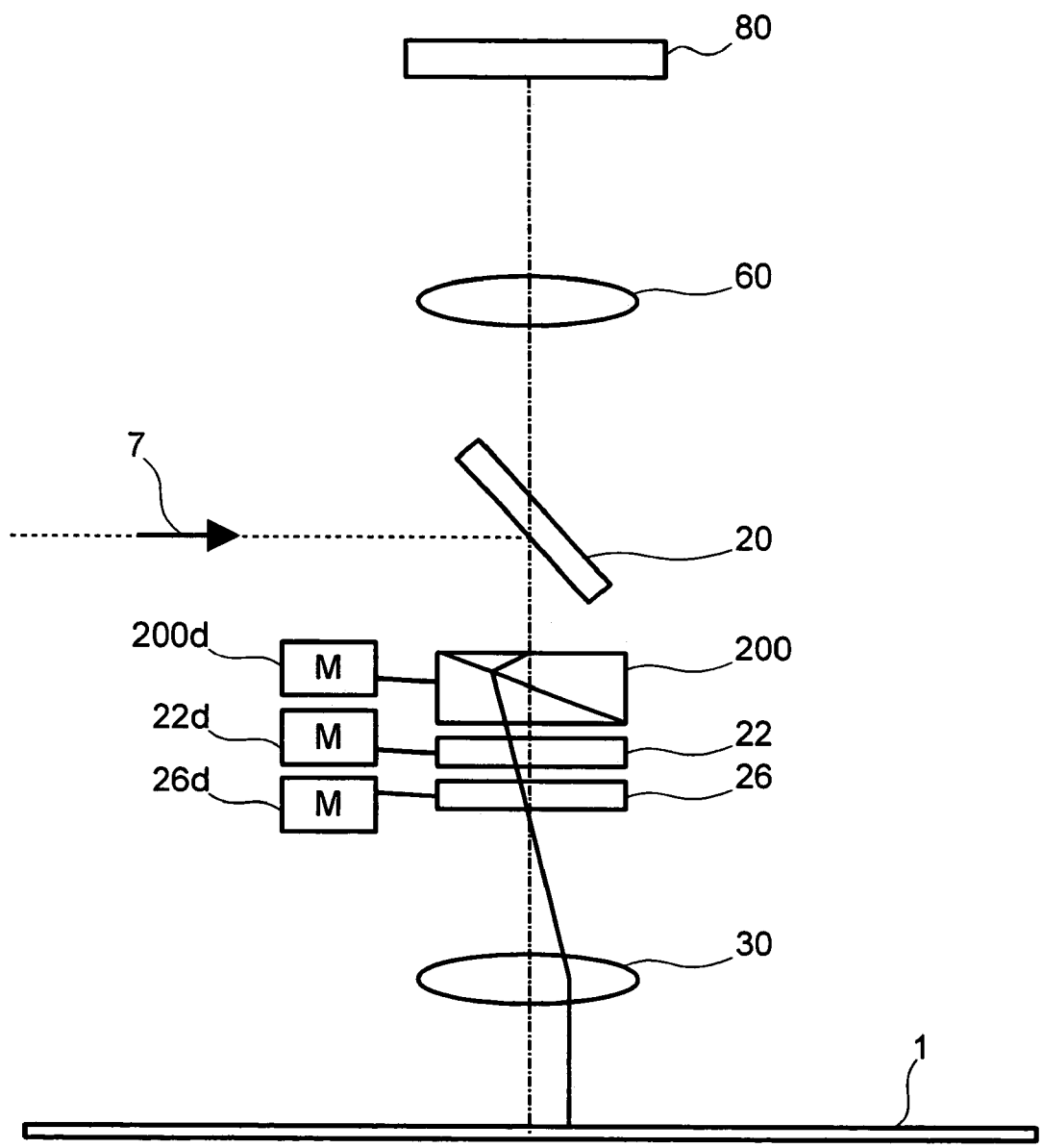
FIG. 17 is a diagram which shows an example of differential interference and an amplitude-reducing detection of zero-order light.

FIG. 17 shows an optical system in which differential interference and elliptical polarization are combined. The linearly polarized light reflected off the PBS 20 enters a birefringent prism 200 and is sheared into two beams of light. The direction in which each polarized light vibrates is rotated by a half-wavelength plate 22 to become elliptically polarized light. The elliptically polarized light illuminating a wafer 1 through an objective lens 30 is regularly reflected off the wafer and is again captured by the objective lens 30. Due to a phase shift, the light regularly reflected off the wafer enters a quarter-wavelength plate 26 again. The light passing through the quarter-wavelength plate 26 becomes linearly polarized light again and enters the half-wavelength plate 22. Further, the two beams of light are turned to be coaxial relative to each other by the birefringent prism 200.

Of the composed vectors in the direction in which coaxial beams of light vibrate, a component of p-polarized light passes through the PBS 20 and is guided into a detection optical path. These beams of light form an image of the wafer 1, through an imaging lens 60, on an image sensor 80. Further, even in the absence of the quarter-wavelength plate 26, since the travelling direction of higher-order diffracted light with respect to zero-order light is different, the higher-order diffracted light vibrates in a different direction with respect to the zero-order light. Therefore, even if the zero-order light is a component of s-polarized light which does not pass through the PBS 20, the higher-order diffracted light has a component which passes through the PBS. Therefore, it becomes possible to enhance the inspection sensitivity by multiplied effects of the following features:

1) Increase in vertical resolution by differential interference; and 2) Increase in horizontal resolution in the detection by enhancing higher-order diffracted light against zero-order light. Further, in order to be able to change the direction of shearing, the birefringent prism 200, the half-wavelength plate 22, and the quarter-wavelength plate 26 are each provided with mechanisms 200d, 22d, and 26d, each of which provides rotation in a horizontal plane about the optical axis.

Figure 18:
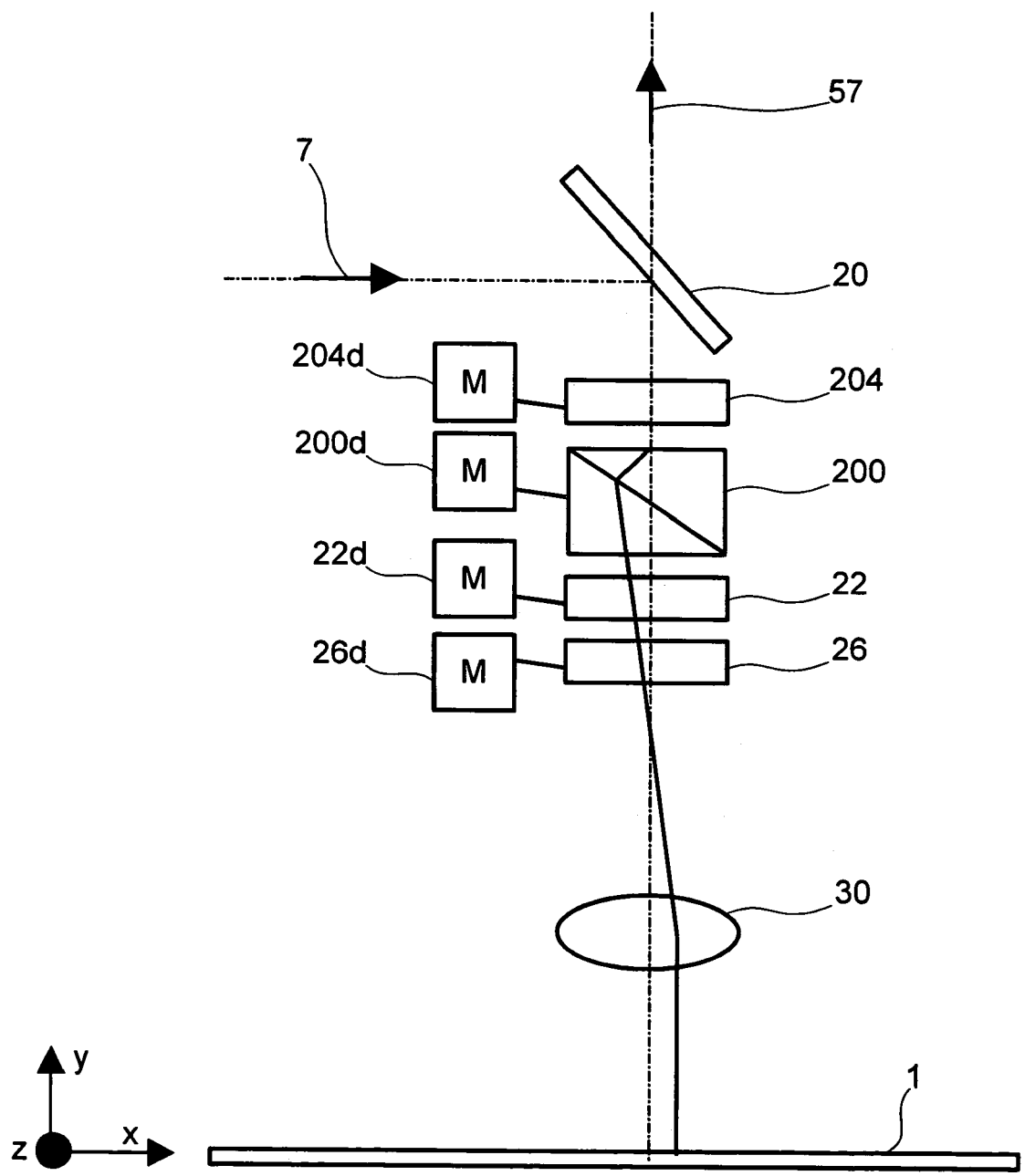
FIG. 18 is a diagram which shows an example of differential interference and an amplitude-reducing detection of zero-order light.

In differential interference, it is possible to effect adjustment to detect a flat portion either in a brightened state or in a darkened state. Particularly, in the case of a wafer 1 in which an SiO2 film is not formed on its surface or there is no inconsistencies in film thickness of the SiO2, the inspection sensitivity can be enhanced when the flat portion is detected brightly. Therefore, a method of adjusting the detecting amount of light of the flat portion will be described with reference to FIG. 18.

Linearly polarized light reflected of f the PBS 20 enters a quarter-wavelength plate 204. For example, the angle formed by the crystal axis of the quarter-wavelength plate 204 and the direction in which the linearly polarized light vibrates is set to 45°. In this case, the light passing through the quarter-wavelength plate 204 becomes circularly polarized light. This circularly polarized light is sheared into two beams by having the light enter a birefringent prism 200. The light passes through a half-wavelength plate 22 and a quarter-wavelength plate 26 to form two beams of elliptically polarized light whose major elliptical axes cross at right angles.

The light having illuminated a wafer 1 through an objective lens 30 enters the quarter-wavelength plate 204 again through the objective lens 30, the quarter-wavelength plate 26, the half-wavelength plate 22, and the birefringent prism 200. In this case, when there is no difference in level of the wafer surface 1, the light passing through the quarter-wavelength plate 204 becomes p-polarized light with respect to the PBS, and the most of the light is guided into the detection optical path 57, forming an optical image on an image surface.

With this configuration, it becomes possible to detect the flat portion in a bright state. Further, corresponding to the ellipticity adjusted by the quarter-wavelength plate 26, the amount of light guided into the detection optical path 57 varies; for example, a greater amount of light is guided into the detection optical path when the crystal axis of the quarter-wavelength plate 26 is in parallel with or perpendicular to the incident polarized light.

Further, each of the quarter-wavelength plate 204, birefringent prism 200, half-wavelength plate 22, and quarter-wavelength plate 26 has a rotary mechanism for effecting rotation about an optical axis (those elements having a numeral with 'd' appended thereto in the drawing).

Further, a component of light that is elliptically polarized by the quarter-wavelength plate 26 propagates along an optical path which is different from the case when illuminated by the birefringent prism 200. Accordingly, the optical image appears as a double image like a ghost. The amount of shift of this double image relates to the amount of shearing, and the intensity of the double image relates to the ellipticity of the quarter-wavelength plate 26. Since the double image is negated during the defect detection when a comparative inspection is being performed, it does not cause a problem.

Further, a condition to detect a flat portion in a darkened state is established by arranging the crystal axis of the quarter-wavelength plate 204 and the direction of vibration of the illuminating light, which is reflected off the PBS and becomes linearly polarized light, in parallel to each other. Further, when expecting a mere differential interference effect, this can be achieved by arranging the lagging phase axis and the leading phase axis so that they are perpendicular to and parallel to the vibration direction (vibration in which two beams cross at right angles) of the polarized light entering the quarter-wavelength plate 26, respectively. Therefore, when expecting an effect of differential interference, the half-wavelength plate 22 and the quarter-wavelength plate 26 are not necessary.

Figure 19:
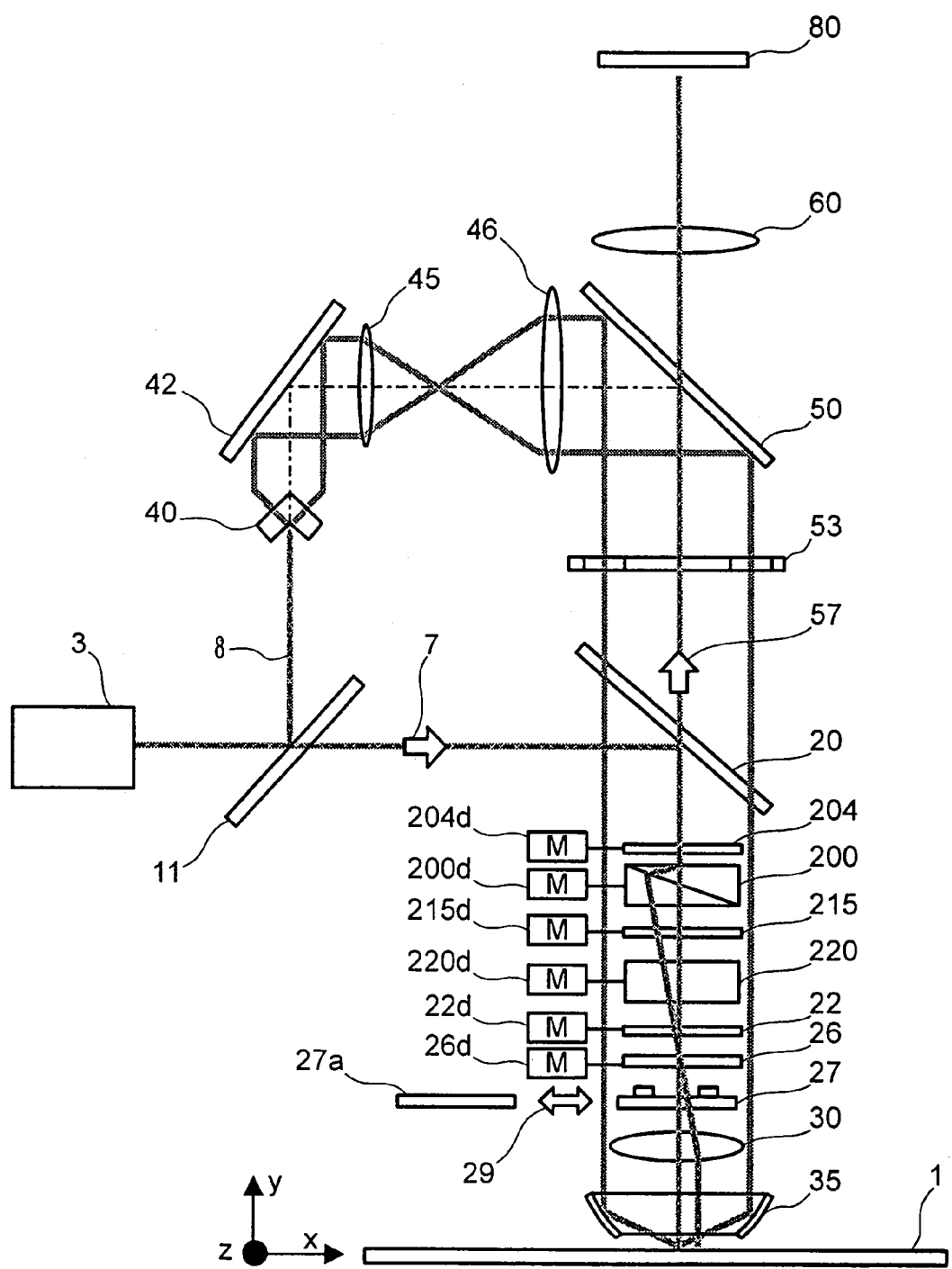
FIG. 19 is a diagram which shows the configuration of an optical system in which differential interference, an amplitude-reducing detection of zero-order light, phase difference detection of zero-order light, and dark-field illumination are available.

FIG. 19 shows an embodiment in which all the configurations described above are put together. The illuminating optical path is divided into a bright-field illuminating optical path 7 and a dark-field illuminating optical path 8, and each of them illuminates a wafer 1. The bright-field illuminating light reflected off the PBS 20 passes through the quarter-wavelength plate 204, the birefringent prism 200, the half-wavelength plate 215, the birefringent prism 220, the half-wavelength plate 22, the quarter-wavelength plate 26, and the zero-order light compatible phase-difference plate 27 (a glass material with high transmissivity of illuminating light is provided with a phase film disposed at a position corresponding to an opening of an aperture diaphragm), and the wafer 1 is illuminated through an objective lens 30 by light that is sheared at right angles into four beams.

In the zero-order light compatible phase-difference plate 27, the aperture diaphragm has a zonal opening, and a phase-difference film is formed in a region corresponding to the opening to add a phase difference π (an optical path of a half of the wavelength). Thus, the phase difference π is given to zero-order light regularly reflected off the wafer, and no phase difference is given to higher-order diffracted light passing through a region having no phase-difference film. Therefore, by disposing a zero-order light compatible phase-difference plate 27, a difference in level of the wafer, which used to be of low contrast without the plate 27, can be detected with higher contrast.

Further, when a highly contrasted image can be detected without the zero-order light compatible phase-difference plate 27, there is no need to provide a zero-order light compatible phase-difference film. In such a case, the zero-order light compatible phase-difference plate 27 is removed from the optical path, and a glass material of even thickness is placed there. In the case of Kohher illumination, the zonal aperture diaphragm must be disposed near a position conjugated to an eye of the objective lens 30.

Therefore, the zero-order light compatible phase-difference plate 27 also must be disposed near the eye of the objective lens 30 or a position conjugated to the eye (a position conjugated to the aperture diaphragm). When disposing a glass plate near the eye, a wave aberration is caused. Therefore, when designing the objective lens 30, it must be designed such that the wave aberration by the zero-order light compatible phase-difference plate 27 is adjusted. Therefore, when the zero-order light compatible phase-difference plate 27 is not necessary, instead of removing it, a mechanism 29 for disposing a glass 27*a* of the same material and thickness must be provided.

According to the above configuration, among the light reflected/diffracted/scattered off the wafer 1, a component of p-polarized light with respect to the PBS 20 is guided into a detection optical path, and it forms an image of the wafer 1 on an image sensor 80 through an image forming lens 60.

The embodiments described above represent some examples of the present invention, and it is easy to predict a combination of them. Therefore, it can be easily conceived that any combination of the configurations set forth shown in the present disclosure falls within the scope of the present invention.

Also, as optical image detection methods described in conjunction with the embodiments, various kinds of optical conditions are given as examples.

Therefore, when inspecting a wafer 1 for the first time, it is time consuming to find an optical condition that is advantageous to the inspection.

Therefore, with respect to each condition of the inspections performed, the following data is accumulated in a database of the OC 95: (1) Inspection sensitivity (the number of defects detected, pseudo defects); (2) Feature amount of detected defects (size, directionality, layer having defects, coordinates of defects, criticality); (3) Feature of wafer to be inspected (design rule, directionality of a major pattern, material quality of a layer to be inspected, existence and non-existence of SiO2 film, feature of a highly critical defect (pattern defect (short circuit, disconnection, etc.), foreign substances, etc.).

When inspecting a wafer of a new kind and process, the time for setting optical conditions can be shortened by automatically selecting recommended conditions corresponding to such information.

As previously described, according to the present invention, it becomes possible to detect a difference in the level of a wafer surface as a difference in brightness by shearing beams of light into two-dimensional directions crossing at right angles and having them differentially interfere with each other.

Further, with respect to conditions with which a flat portion is detected in a darkened state, inconsistencies in brightness (not affecting a device critically) due to thin-film interference through a transparent film, such as an SiO2 film formed on the wafer, can be reduced, and the inspection sensitivity can be enhanced. This effect can be achieved also by dark-field illumination.

Further, when grains (irregularities, etc.) formed in metal wiring, etc. do not affect a device critically, the contrast can be kept low by bright-field/dark-field-combined illumination.

Further, a pattern contrast can be enhanced by elliptically polarized illumination which forms an optical image by reducing the amplitude of zero-order light.

Still further, it is possible to detect an image with low contrast in a highly contrasted state by imparting a phase difference to zero-order light with respect to higher-order diffracted light.

Thus, it becomes possible to achieve a highly sensitive inspection by selecting a condition advantageous to each of the objects to be inspected of various types and processes from the conditions described above.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and ranges of equivalency of the claims are therefore intended to be embraced therein.

What is claimed is:

1. A method of inspecting for defects comprising the steps of:
    dividing illuminating light emitted by a light source into four beams to have different polarization characteristics with each other;
    applying the divided four beams having different polarization characteristics with each other to a sample to illuminate the sample through an objective lens;
    composing the applied of said divided four beams that have been reflected off said sample and passed through said objective lens into a composed beam of light;
    forming an image of the sample by the composed beam of light through an image forming optical system;
    obtaining an image of said sample by detecting the image of the composed beam with a sensor; and
    detecting defects of said sample by comparing the obtained image with a reference image stored in a memory to extract a difference between them.

2. A method of inspecting for defects according to claim 1, wherein said illuminating light is divided into four beams by using a first birefringent prism and a second birefringent prism in such a way that the light emitted from said light source is divided into two beams by the first birefringent prism, and each of said divided two beams is further divided into two by the second birefringent prism.

3. A method of inspecting for defects according to claim 1, wherein the illuminating light is further applied obliquely to said sample from outside of said objective lens in the step of illuminating said sample.

4. A method of inspecting for defects according to claim 1, wherein, with respect to an electric field vector of said composed beam of light, an optical image is formed by reducing the amplitude of the light reflected off a flat portion of the sample in the step of obtaining said image.

5. A method of inspecting for defects according to claim 1, comprising at least one of:
   storing information regarding the defects detected by the detecting operation, for future use; and
   using information regarding the defects detected by the detecting operation to analyze at least one defect of said sample.

6. A method of inspecting for defects comprising the steps of:
   illuminating a substrate having patterns formed on its surface with four polarized beams, through an objective lens, whose directions of electric field vectors are different with each other;
   imaging said substrate by forming an optical image on a sensor surface through an image forming optical system with a composed beam of light which is composed with lights reflected from said substrate by the illuminating and entered said objective lens during the illumination; and
   detecting defects of said sample by comparing the obtained image with a reference image stored in a memory to extract a difference between them.

7. A method of inspecting for defects according to claim 6, wherein an optical image is formed by adjusting the amount of zero-order light of the light reflected from said substrate and the directions of electric field vectors in said step of imaging.

8. A method of inspecting for defects according to claim 6, comprising at least one of:
   storing information regarding the defects detected by the detection operation, for future use; and
   using information regarding the defects detected by the detection operation to analyze at least one defect of said sample.

9. A method of inspecting for defects comprising the steps of:
   illuminating a substrate having patterns formed on its surface with a light emitted from a light source;
   imaging the illuminated substrate through an image forming optical system; and
   detecting defects of said sample by comparing the obtained image with a reference image stored in a memory extract a difference between them,
   wherein, in said illuminating step, bright-field illumination and a combination of bright-field and dark-field illumination are switched for illuminating said substrate in accordance with a type of a pattern formed on the surface of said substrate, and a light used in the bright-field illumination includes at least four beams of light each of which are arranged to have mutually different polarization state, and in said imaging step, the four beams of light of the bright-field illumination reflected from said substrate are composed into a composed beam of light used for the imaging.

10. A method of inspecting for defects according to claim 9, wherein said bright-field illumination used in said illuminating step is the one in which differential interference is available.

11. A method of inspecting for defects according to claim 9, wherein the light used in the bright-field illumination and the light used in the dark-field illumination are emitted from the same light source in said illuminating step.

12. A method of inspecting for defects according to claim 9, comprising at least one of:
   storing information regarding the defects detected by the detection operation, for future use; and
   using information regarding the defects detected by the detection operation to analyze at least one defect of said sample.

13. An apparatus for inspecting for defects comprising:
   a light source;
   illuminating means illuminating a substrate having patterns formed thereon with light that has been emitted from the light source and divided into four beams;
   image forming means for composing each of said four beams after being reflected off said substrate being illuminated by the illumination means and forming an optical image of said illuminated substrate;
   image obtaining means detecting an optical image of said substrate as formed by the image forming means and obtaining an image of said substrate; and
   defect detecting means processing the image obtained by the image obtaining means and detecting defects on said substrate;
   wherein said illuminating means has a first polarization adjusting part adjusting the polarizing direction of the four divided beams illuminating said substrate, and said image forming means has a second polarization adjusting part adjusting the polarization direction of the beam made by composing each reflected light of said four beams from said substrate.

14. An apparatus for inspecting for defects according to claim 13, wherein said illuminating means comprises two birefringent prisms, the light emitted from said light source is divided into two beams by one of the two birefringent prisms, and each of said two divided beams is further divided into two beams by the other birefringent prism.

15. An apparatus for inspecting for defects according to claim 13, wherein said illuminating means comprises two birefringent prisms, the light emitted from said light source is divided into two beams by one of the two birefringent prisms, and each of said two divided beams is further divided into two beams by the other birefringent prism.

16. An apparatus for inspecting for defects comprising:
   a light source;
   illuminating means illuminating a substrate having patterns formed thereon with light that has been emitted from the light source and divided into four beams;
   image forming means for composing each of said four beams after being reflected off said substrate being illuminated by the illumination means and forming an optical image of said illuminated substrate;
   image obtaining means detecting an optical image of said substrate as formed by the image forming means and obtaining an image of said substrate;
   defect detecting means processing the image obtained by the image obtaining means and detecting defects on said substrate; and
   a branching means branching the light emitted from said light source, wherein one of the beams of light branched by the branching means is allowed to enter said illuminating means, and the other one of the beams of light branched by the branching means is allowed to enter an oblique illuminating means illuminating said substrate obliquely.

17. An apparatus for inspecting for defects comprising:
   a light source;
   a branching means branching the light emitted from the light source into two optical paths;
   a bright-field illuminating means illuminating a substrate having patterns formed on its surface with one of the beams of light branched by said branching means through an objective lens;

a dark-field illuminating means illuminating said substrate obliquely from outside of said objective lens with the other one of the beams of light branched by said branching means;

an image forming means forming an optical image of said substrate with the light reflected off said substrate illuminated by said bright-field illuminating means and said dark-field illuminating means and passing through said objective lens;

an image obtaining means obtaining an image of said substrate by detecting an optical image of said substrate formed by the image forming means; and a defect detecting means processing the image obtained by the image obtaining means and detecting defects on said substrate.

18. An apparatus for inspecting for defects according to claim 17, wherein said bright-field illuminating means comprises a beam dividing part dividing the light branched by said branching means into four beams.

19. An apparatus for inspecting for defects according to claim 17, wherein said bright-field illuminating means comprises a first polarizing adjusting part adjusting a polarizing direction of the light branched by said branching means and said image forming means comprises a second polarizing adjusting part adjusting a polarizing direction of the light reflected off said substrate illuminated by said bright-field illuminating means and said dark-field illuminating means and passing through said objective lens.

* * * * *